US009241797B2

(12) United States Patent
McKay

(10) Patent No.: US 9,241,797 B2
(45) Date of Patent: Jan. 26, 2016

(54) BONE DELIVERY SYSTEMS INCLUDING HOLDING AND FILLING DEVICES AND METHODS

(71) Applicant: WARSAW ORTHOPEDIC, INC., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/582,600

(22) Filed: Dec. 24, 2014

(65) Prior Publication Data

US 2015/0119858 A1    Apr. 30, 2015

Related U.S. Application Data

(63) Continuation of application No. 13/438,590, filed on Apr. 3, 2012, now Pat. No. 8,926,622.

(51) Int. Cl.
*A61M 31/00* (2006.01)
*A61F 2/28* (2006.01)
*A61F 2/30* (2006.01)

(52) U.S. Cl.
CPC ....... *A61F 2/2846* (2013.01); *A61F 2002/2835* (2013.01); *A61F 2002/30462* (2013.01); *A61F 2002/30586* (2013.01); *A61F 2002/30588* (2013.01); *A61F 2002/30729* (2013.01); *A61F 2210/0004* (2013.01)

(58) Field of Classification Search
CPC combination set(s) only.
See application file for complete search history.

(56) References Cited

U.S. PATENT DOCUMENTS

| | | | |
|---|---|---|---|
| 5,202,021 A | 4/1993 | Griffin et al. | |
| 6,294,187 B1 | 9/2001 | Boyce et al. | |
| 6,440,444 B2 | 8/2002 | Boyce et al. | |
| 6,478,825 B1 | 11/2002 | Winterbottom et al. | |
| 6,696,073 B2 | 2/2004 | Boyce et al. | |
| 7,083,648 B2 | 8/2006 | Yu et al. | |
| 7,955,292 B2 * | 6/2011 | Leroy | A61B 17/00234 206/216 |
| 8,042,688 B2 | 10/2011 | Parks et al. | |
| 2005/0251267 A1 | 11/2005 | Winterbottom et al. | |
| 2005/0283255 A1 | 12/2005 | Geremakis et al. | |
| 2006/0052879 A1 | 3/2006 | Kolb | |
| 2007/0088443 A1 | 4/2007 | Hanssen et al. | |
| 2007/0098756 A1 | 5/2007 | Behnam | |
| 2007/0110820 A1 | 5/2007 | Behnam | |
| 2007/0191963 A1 | 8/2007 | Winterbottom et al. | |
| 2009/0130173 A1 | 5/2009 | Behnam et al. | |
| 2009/0192474 A1 | 7/2009 | Wei et al. | |
| 2009/0234277 A1 | 9/2009 | Wei et al. | |
| 2009/0240255 A1 | 9/2009 | McKay et al. | |
| 2010/0203155 A1 | 8/2010 | Wei et al. | |
| 2011/0054408 A1 | 3/2011 | Wei et al. | |

* cited by examiner

*Primary Examiner* — Sameh Boles
(74) *Attorney, Agent, or Firm* — Sorell Lenna & Schmidt LLP

(57) ABSTRACT

A delivery system comprising a biodegradable single or multi compartment covering is provided. The covering can be a mesh bag including a pre-attached detachable holding member surrounding the opening of at least one compartment and a pre-attached removable filling member configured to fit within the opening of the at least one compartment. The opening of the bag can include a closing member. The pre-attached detachable holding member can be a collar including finger grips and is used to hold the bag in one position while filling it. In some embodiments, the pre-attached detachable filling member can be a funnel for loading the mesh bag with bone graft material. Once the covering is filled, the holding member and filling member can be removed and the covering is closed with a closing member such as a drawstring. A method of treatment utilizing the delivery system is also provided.

14 Claims, 2 Drawing Sheets

BONE DELIVERY SYSTEMS INCLUDING HOLDING AND FILLING DEVICES AND METHODS

This application is a continuation application of U.S. patent application No. 13/438,590 filed Apr. 3, 2012, entitled "BONE DELIVERY SYSTEMS INCLUDING HOLDING AND FILLING DEVICES AND METHODS." This entire disclosure is incorporated herein by reference into the present disclosure.

FIELD

Delivery systems for delivering a substance or material to a surgical site are provided. More particularly, delivery systems comprising a covering, detachable pre-attached holding and filling member for adding material to the covering are provided.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damaged cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. Further, the implant is substantially complete at the time of implantation and thus provides little ability for customization, for example by the addition of autograft.

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Demineralized bone matrix ("DBM") implants have been reported to be particularly useful. Demineralized bone matrix is typically derived from cadavers. The bone is removed aseptically and/or treated to kill any infectious agents. The bone is then particulated by milling or grinding and then the mineral components are extracted for example, by soaking the bone in an acidic solution.

Current DBM formulations have various drawbacks. First, while the collagen-based matrix of DBM is relatively stable, the active factors within the DBM matrix are rapidly degraded. The osteogenic activity of the DBM may be significantly degraded within 24 hours after implantation, and in some instances the osteogenic activity may be inactivated within 6 hours. Therefore, the factors associated with the DBM are only available to recruit cells to the site of injury for a short time after transplantation. For much of the healing process, which may take weeks to months, the implanted material may provide little or no assistance in recruiting cells.

Attempts to overcome these problems have lead researchers to utilize delivery systems such as enclosed polymer mesh bags to release DBM at a surgical site. However, any additional bone graft material, such as autologous bone or growth factors, would have to be placed underneath or on top of the DBM mesh bag which approach does not always induce new bone formation.

Thus, there is a need to improve the efficacy and consistency of DBM delivery systems by mixing the DBM particles/fibers with other bone graft materials such as autologous bone and other bioactive agents throughout the mesh bag prior to or during the surgical procedure. It would therefore be desirable to provide delivery systems that are configured to enhance bone growth.

SUMMARY

A delivery system is provided that allows live cells and other bioactive agents to be in close contact with DBM particles/fibers so as to induce bone growth in the mesh bag and throughout the graft material rather than inducing bone growth primarily along the surface of the polymer mesh bag.

In various embodiments, a delivery system comprising a biodegradable covering configured for implantation into a bone defect site is provided. The covering may include a single or multi-compartment structure. In various embodiments, the covering includes at least one compartment defining an opening which can have a pre-attached closing member, a pre-attached detachable holding member surrounding the opening of the at least one compartment and a pre-attached removable filling member configured to fit within the opening of the at least one compartment for loading the at least one compartment with at least one substance.

In some embodiments, the pre-attached detachable holding member of the covering can be a collar having a circumference of round or oval shape that is configured to be placed around the diameter of the bag.

In certain embodiments, the pre-attached detachable collar contains a gripping member selected from at least two finger grips or finger depressions or a combination thereof. The gripping member can be part of the collar or can be detachable from the collar.

In some embodiments, the pre-attached removable filling member of the covering includes a funnel, a spoon, a spatula or a syringe.

In various embodiments the closing member can be cooperatively attached with the gripping member, such that the at least one compartment can close upon disengaging the gripping member from the collar.

In certain embodiments, the collar including the gripping member, the funnel or all include injected molded plastic or a material selected from bioerodible polymers, bioabsorbable polymers, biodegradable biopolymers, synthetic polymers, copolymers or combinations thereof.

In some embodiments, the detachable collar is pre-attached to the proximal surface of the covering or the at least one compartment through pull-strings or compression fittings or a combination thereof such that the collar can be easily disengaged from the covering or the at least one compartment.

In various embodiments, the closing member includes drawing strings, stitches, sutures, heat seals, adhesive seals, pressure fittings or combinations thereof. The drawstring can be slidably received in a casing extending about the periphery of the opening of the at least one compartment and have two apertures positioned proximate each other so that when the end portions of the drawstring are pulled out of the drawstring casing through the two apertures, the periphery of at least one compartment gathers to reduce the opening of the at least one compartment in size sufficiently to enclose the at least one substance therein. The at least one substance comprises autograft, allograft, demineralized bone matrix fibers and demineralized bone matrix chips in a 30:60 ratio or a combination thereof.

In other aspects, a delivery system comprising a covering configured for implantation into a bone defect site is provided, wherein the covering has at least one compartment comprising an elongated containment having a first end and a second end opposite each other. One end of the elongated containment defines an opening, and there is a closing member proximate to the opening. The containment further includes a pre-attached detachable holding member surrounding the opening of the containment proximate to the closing member. The pre-attached holding member, such as a collar is configured to include a gripping member such as finger grips or finger depressions on opposite sides of the collar. The containment also includes a pre-attached removable filling member, for example a funnel configured to fit within the opening of the elongated containment.

In various embodiments, a method is provided for treating a bone defect in a patient in need of such treatment, the method comprising implanting into the bone defect all or at least a portion of a covering, the covering being porous and comprising at least one compartment available for filling with allograft or other bone graft material prior to a or during a surgical procedure. The at least one compartment defines an opening having a pre-attached closing member. The at least one compartment also includes a pre-attached detachable holding member surrounding the opening of the at least one compartment and a pre-attached removable filling member configured to fit within the opening of the at least one compartment for loading with at least a first substance.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

DETAILED DESCRIPTION

Definitions

Figure 1:
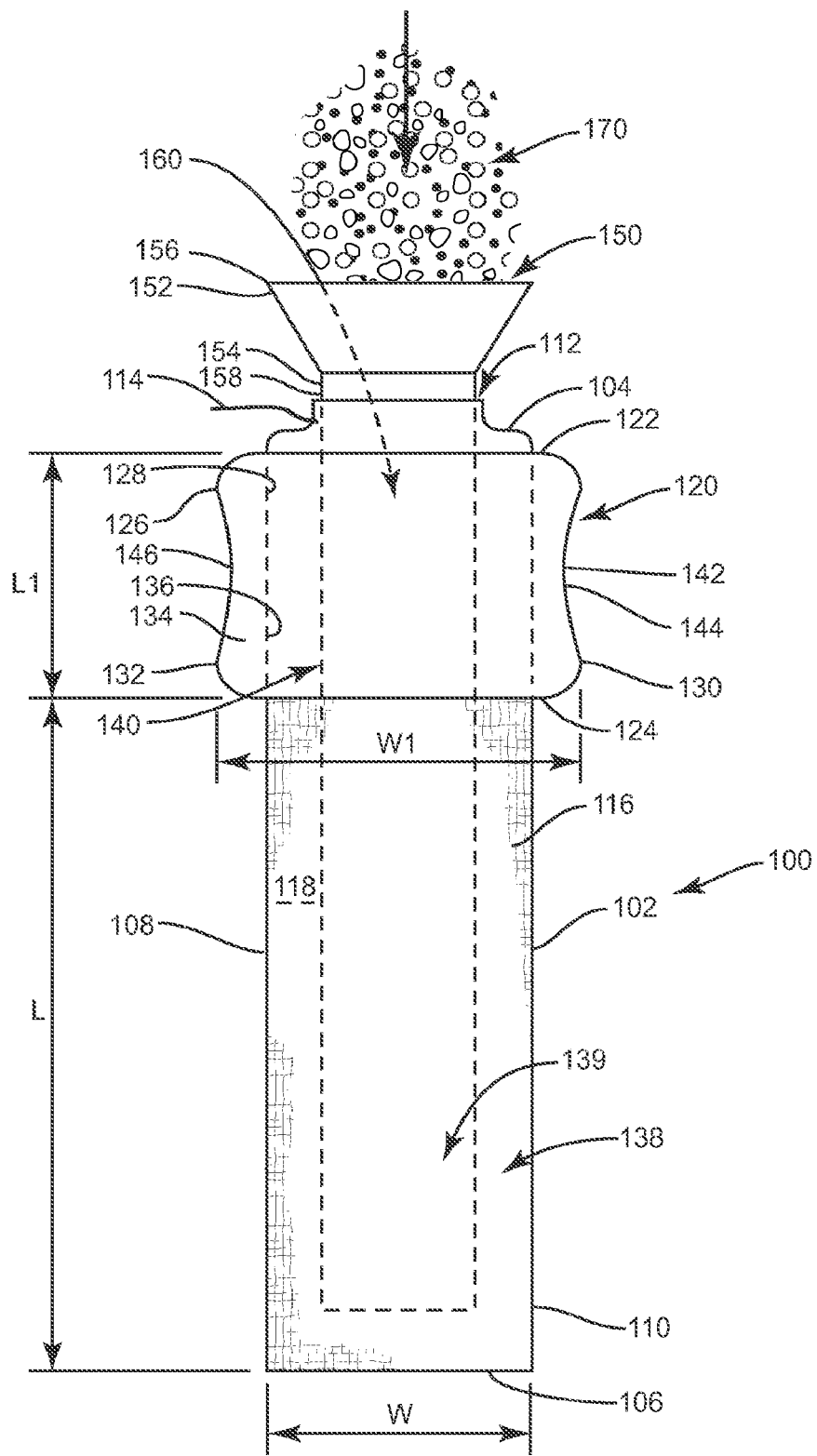
FIG. 1 depicts a side view of a delivery system according to an aspect of the present application.

It is noted that, as used in this specification and the appended claims, the singular forms "a," "an," and "the," include plural referents unless expressly and unequivocally limited to one referent. For example, reference to "a covering" includes one, two, three or more coverings.

Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the application.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this application and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the delivery systems described herein may obviously be disposed in different orientations when in use.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Introduction

A delivery system for delivery of a substance or material to a surgical site is provided. In various embodiments, the delivery system comprises an implantable covering, for example a mesh bag, having at least one compartment configured to receive at least a first substance, for example, autograft chips for delivery to a surgical site. The at least one compartment has a top end and a bottom end opposite each other wherein at least one end defines an opening having a closing member and is configured to receive a removable filling member utilized to fill the at least one compartment with allograft chips or other material for delivery to a surgical site. The implantable covering also includes a pre-attached detachable holding member surrounding the opening of at least one end of the covering, the detachable holding member positioned proximate to the closing member of the covering.

Generally, the covering may be a single or multi-compartment structure capable of at least partially retaining a substance provided therein until the covering is placed at a surgical site as more particularly described in United States published application No. 20100203155 incorporated herein by reference as if set forth in full. In some embodiments, the covering may be substantially non-expandable or minimally deformable. In some embodiments, the covering may be a temporary covering wherein the covering is substantially resorbable. For example, in some embodiments, the covering may be formed of a material that is substantially resorbed within 2 weeks, within 4 weeks, within 12 weeks, or within other suitable time frame. Accordingly, in some embodiments, a delivery system including the covering may be a temporary delivery system. The covering may include one or more attachment mechanisms for retaining the covering at the surgical site. The attachment mechanism may be a mechanical attachment mechanism, a physical attachment mechanism, a biological attachment mechanism or a chemical attachment mechanism, or may employ combinations of these. The attachment mechanism may be used to attach the covering to skeletal or soft tissue proximate the surgical site.

In some embodiments, the covering may be used for containment of particulate or morselized materials (the substance provided in the covering), optionally to provide a focus or concentration of biological activity. In some embodiments, the covering may be used for containment of a substance one or more of bone particles, bone fibers, other osteoinductive or osteoconductive materials, BMP, antibiotics, or other materials.

In some embodiments, the covering may be used for maintaining materials (the substance provided in the covering) in spatial proximity to one another, possibly to provide a synergistic effect. In some embodiments, the covering may be used to control availability of a substances provided within the covering to cells and tissues of a surgical site over time. In some embodiments, the covering may be used for delivery through a limited opening, such as in minimally invasive surgery or mini-open access. In some embodiments, the covering may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering may contain a substance or material such as a graft material. The covering limits, and in some embodiments eliminates, graft migration and maintains graft density. The delivery system, with contained substance or material, may be configured to conform to surrounding bony contours or implant space. In some embodiments, the delivery system provides a pathway for healing/cell penetration and tissue ingrowth. Thus, the covering may facilitate transfer or diffusion of materials into and out of the covering. For example, the covering may facilitate diffusion from the covering of a substance provided within the covering or may facilitate diffusion into the covering of materials in the surgical site, such as cells and tissues, into the covering. The covering may be configured to permit diffusion of some materials while substantially preventing diffusion of other materials. Further, in various embodiments, the covering may be configured such that diffusion is permitted into or out of certain portions of the covering but not other portions of the covering. In some embodiments, the covering may merely retain a substance at the surgical site.

The covering may have a single compartment or may have a plurality of compartments. Thus, in one embodiment, the covering is dual-compartment and comprises first and second compartments. A first substance may be provided in the first compartment and a second substance may be provided in the second compartment. The second compartment may be adjacent to, apart from, inside, or surrounding the first compartment. Materials forming the first compartment and the second compartment may be the same or may be different. Selection of materials, positioning of the compartments, and other factors relating to the first and second compartments may be chosen to achieve simultaneous or sequential delivery or release of a substance or substances.

In various embodiments, a portion of the covering, for example, one compartment of a multi-compartment covering or the entire covering may be empty and available to be filled prior to or during the surgery. During the surgery, the surgeon may remove autograft from the patient and place it in the substantially empty compartment. In certain embodiments, such placement can be advanced by utilizing a bone delivery system as described herein which includes a pre-attached but detachable holding member that allows the surgeon to hold the covering in an upright position while filling it with autograft chips or other bone grafting materials using removable filling member, for example, a funnel, also pre-attached to the covering or the holding member. The pre-attached holding member, for example a collar, can be attached to the covering by pull-string sutures, compression fittings or other similar attachments. As a result, the pre-attached holding member can be easily disengaged either by pulling out the suture string or releasing the pressure fittings. In certain embodiments in order to steady further the covering which is frequently soft and flexible, the pre-attached holding member further comprises at least two finger grips positioned to enable the surgeon to grip the holding member firmly while filling the covering. In various other embodiments, the delivery system further includes a removable filling member also pre-attached to the covering in order to facilitate its loading with autograft or bone grafting material. Once the covering, for example a mesh bag, has been filled with the desired amount of autograft or other bone grafting material, the pre-attached holding member and pre-attached filling member are easily disengaged and the bag can be closed by pulling a pre-attached drawstring or other closing member as further described herein below. At its ends, the pre-attached drawstring also includes easy to catch buttons so that the drawstring can be easily tied or knotted to confine the autograft or other bone graft material into the covering. While the holding and filling member can be made from injected molded plastic to provide sufficient rigidity, in certain embodiments, biodegradable materials are also contemplated.

Covering, Holding and Filling Devices

FIG. 1 illustrates a bone delivery device system having a covering 102, a holding device in the shape of a collar 120 and a funnel 150.

Covering 102 comprises a biocompatible implant material 170 and includes a proximal surface 116, a distal surface 118, top end 104, bottom end 106, side walls 108, and 110. In the illustrated covering 102, a rectangular configuration is provided. Covering 102 comprises a length, width and cross section which may vary depending on the application for the covering. The cross section can be tubular or cylindrical, and in alternative embodiments, any cross-sectional shape, such as a generally circular, oval, rectangular, generally square, generally star, or any other suitable shape may be used. In the embodiment shown in FIG. 1, the covering 102 comprises a mesh material and can be a mesh bag. Within these coverings or mesh bags, there can be provided a particulated substance such as milled bone or DBM particles/fibers, wherein the ratio of autograft, allograft, DBM fibers or DBM chips to autograft, allograft, DBM fibers or DBM chips is between 25:75 and 75:25. In one embodiment, the ratio of DBM fibers to DBM chips is about 30:60.

In other embodiments, covering 102 includes a length L, defined as the dimension of side walls 108 and 110 in a first direction, a width W defined by the dimension of bottom and top ends 104 and 106 in a first direction, and a thickness T (not shown) defined by the dimension of side walls 108 and 110 in a second direction generally perpendicular to the first directions noted above.

In certain embodiments, the length L of the overall implant body 100 will range from about 1 cm to about 15 cm, the width W will range from about 1 cm to about 20 cm, and the thickness T will range from about 0.5 cm to about 9 cm. Length L may range from about 2.5 to about 8 cm, width W may range from about 2.5 to about 8 cm, and thickness T may range from about 1 to about 10 cm.

As to volume, advantageous implant bodies 100 can have a total volume of at least about 2 cubic centimeters (cc), e.g. in the range of about 2 cc to about 100 cc, and more typically in the range of about 10 cc to about 50 cc, although both smaller and larger overall volumes may also be used.

Figure 2:
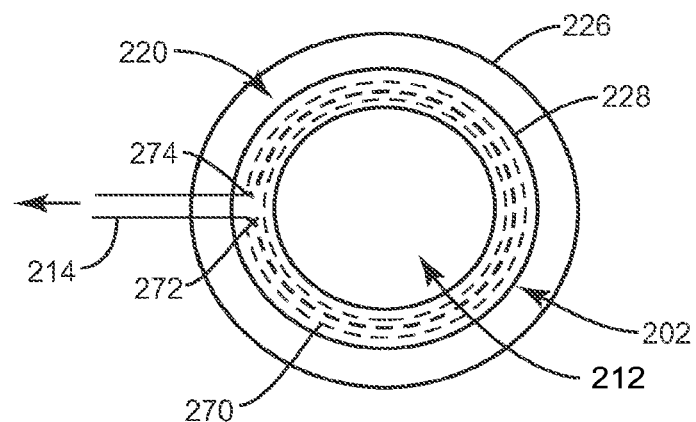
FIG. 2 depicts a top view of a delivery system according to another aspect of the present application.

In various embodiments, top end 104 of covering 102 defines an opening 112 and closing member, such as drawstrings 114 proximately located to opening 112. As illustrated in FIG. 2, in an embodiment of this disclosure, drawstrings 214 are positioned around the perimeter of covering 202 proximate opening 212 of covering 202 slidably received in casing or sleeve 270 so that when the end portions of the drawstring 214 are pulled out of the drawstring casing 270 through the two apertures 272, 274, the perimeter of covering 202 gathers adjacent the casing to permit the perimeter of covering 202 to reduce in size sufficiently to enclose the autograft chips or other graft material therein. FIG. 2 also depicts holding member or a collar 220 which has an outside perimeter 226 and an inside perimeter 228.

Figure 3:
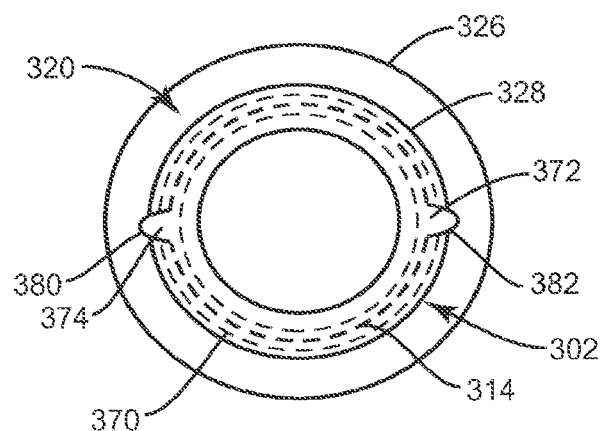
FIG. 3 depicts a top view of a delivery system according to another aspect of the present application.

In another embodiment, as illustrated in FIG. 3, drawstring 314 can be continuous, slidably received in casing 370 and has two loops 380, 382 which extend as oppositely disposed segments around the outside perimeter of the covering 302 at apertures 372, 374 of casing 370. Upon pulling loops 380 and 382, drawstring 314 gathers the perimeter of covering 302 adjacent casing 370 to permit the perimeter of covering 302 to reduce in size sufficiently to enclose the autograft chips or other graft material therein. FIG. 3 also depicts holding member or collar 320 which has an outside perimeter 326 and an inside perimeter 328.

In various other embodiments, the drawstrings used to close the opening of the covering can be wires made of nitinol or any other shape memory alloy. For example nitinol wires can be slidably received in the casing around the perimeter of the opening of the cover and upon the removal of the funnel, the nitinol wires would relapse to a closed position thereby securing the allograft chips or other graft material inside the covering.

With further reference to FIG. 1, collar 120 has a top rim surface 122 and a bottom rim surface 124, an outer surface 134 and an inner surface 136 (shown in phantom) each having an outside perimeter 126 and an inside perimeter 128. Collar 120 also includes side walls 130 and 132. At the top rim surface 122, collar 120 defines an axial access channel 140 extending through the length of the collar to the bottom rim surface 124 and configured to receive covering 102 at a position proximate closing member (e.g., drawstring) 114 of covering 102. Like covering 102, collar 120 has length L1 defined by top and bottom rim surfaces, 122 and 124, a width W1 defined by side walls 130 and 132 in a first direction and a thickness T1 defined by the outside perimeter 126 and inside perimeter 128 in a second direction generally perpendicular to the first direction noted above.

In certain embodiments, the length L1 of the collar 120 will range from about 0.5 cm to about 7 cm, the width W1 may range from about 0.5 cm to about 25 cm and the thickness T1 from about 0.5 cm to about 7 cm.

Collar 120 has an outer surface 134 and an inner surface 136. Between inner surface 136 of collar 120 and proximal surface 116 of implantable covering 102, there are compression fittings or pull-string sutures (not shown in FIG. 1) for attaching covering 102 to collar 120. Collar 120 can be easily disengaged from covering 102 by simply pulling the string sutures or releasing the compression fittings.

In other embodiments, in order to steady further covering 102 which is frequently soft and flexible, pre-attached collar 120 further comprises finger grips 142 positioned on outer surface 134 of collar 120 in depressions 144 and 146 to enable the surgeon to grip collar 120 firmly while filling the covering. Depressions 144, 146 positioned on the outside surface of collar 120 provide traction and are adapted to receive finger grip indentations (not shown in FIG. 1) to enable the user to grip the collar in a firm and steady manner between the user's thumb and index finger or with fingers of both hands, if so desired.

Delivery system 100 also includes a filling member, such as a funnel 150, in some embodiments detachably pre-attached either to collar 120 or, in other embodiments to covering 102. Funnel 150 has a head portion 152 and a neck portion 154 configured to be received within covering 102. Funnel 150 defines an axial access channel 160 contiguous to and extending into axial access channel 140 of collar 120. Generally, it is contemplated that the top circumference 156 of funnel 150 and the neck circumference 158 can be varied ranges depending on the application. It is contemplated that circumferences 156 and 158 are sufficient in size to enable funnel 150 to receive allograft chips and other graft material to allow for the filling of covering 102 either by gravity or with the help of a plunger. Additionally, it is contemplated that the head and neck of funnel 150, both include wider or narrower funnel shape configurations as would generally occur to one skilled in the art to perform its load assisting function. In various embodiments, neck 154 of funnel 150 is also detachably attached to either collar 120 or covering 102 via pull-string sutures or compression fittings and can be easily disengaged either by pulling out the string sutures or releasing the pressure fittings.

Covering Material

The covering may comprise a structural material and, in some embodiments, a functional material. The structural material may comprise a mesh material, a polymeric material, or other. The functional material may comprise, for example, a radiopaque material, a bacteriocidal material, or other material.

In various embodiments, in accordance with the specific application for which the covering is being used, the covering may be rigid, may be flexible, may be non-elastic, or may be elastic. The covering material may be braided, woven, non-woven shape memory, particulate, threaded, porous, or non-porous. In some embodiments, the covering comprises a pouch with demineralized bone material disposed in the pouch uniformly or in discrete positions within the pouch.

The covering may participate in, control, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties that may be adjusted include thickness, permeability, porosity, strength, flexibility, elasticity, and others of the covering material. It is to be appreciated that some of these properties may depend on others. For example, the thickness and porosity of the material may contribute to its strength, flexibility, and elasticity.

In some embodiments, the covering may be porous to fluid and/or cells, may be biocompatible, and may be resistant to rupture (including should the substance provided therein swell). In some embodiments, the covering with the substance provided therein may be loadbearing. The covering may be resorbable or non-resorbable. The covering may provide increased handling properties, may have irrigation resistance, and/or may support cellular penetration. Flexibility of the covering may be selected to suit particular applications. In some applications, it may be desirable to have a flexible covering.

If the covering is made from a resorbable material, the covering degrades and disappears after a period of time. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells for the inside of the covering (e.g. approximately 0.45 microns) and only allow diffusion of small molecules (proteins and hormones). Thus, the covering may act to control access to the interior of the delivery system by cells. In embodiments comprising more than one compartment, characteristics of the covering material may be varied between compartments. Generally, the porosity, flexibility, strength, or any other characteristic of one compartment may vary from that characteristic of the other compartment.

The covering may be formed of a resorbable or nonresorbable, natural or synthetic biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments, or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as autograft, demineralized bone matrix, or others disclosed herein.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc-aluminum-nickel alloy, copper-aluminum-nickel alloy, or nickel-titanium (NiTi) alloy. Reinforcing materials such as cortical bone, calcium phosphates, may also be incorporated into the structure of the covering to reinforce it.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers. The coating may be selected such that it has a resorption time wherein it is resorbed by the body and the material within the covering is permitted to exit through openings in the covering.

A covering according to an aspect of the present application may comprise at least one of bioerodible polymers, bioabsorbable polymers, biodegradable biopolymers, synthetic polymers, copolymers and copolymer blends or combinations thereof. Exemplary materials may include biopolymers and synthetic polymers such as human skin, human hair, bone sheets, collagen, fat, thin cross-linked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

Advantageously, a covering according to an aspect of the present application utilizes polymer materials, which provide increased shelf life and further impart and/or improve moisture and/or radiation resistance. Accordingly, a covering provides improved stability, is resistant to environmental degradation, and provides increased durability to e.g., sterilization procedures.

Exemplary materials may include polymeric material (for example, see U.S. Pat. Nos. 6,696,073, 6,478,825, 6,440,444, and 6,294,187 and U.S. Patent Publications Nos. 2006/0216323 and 2005/0251267, all herein incorporated by reference in their entirety); woven material and braided material (for example, see U.S. Patent Publication No. 2005/0283255, herein incorporated by reference in its entirety); non-woven; shape memory material; using outer particles to contain inner particles; attach particles to threads; add porosity to mesh fibers; non-porous materials; non-porous materials. In some embodiments, materials may be used for portions of the covering, such as for a compartment of the covering, which may be substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly (glycolic acid) (PGA), poly(lactic acid-glycolic acid) (PLGA), polydioxanone, PVA, polyurethanes, polycarbonates, and others. Other suitable materials include carbon fiber, metal fiber, and various meshes. In other embodiments, the covering may comprise non-woven material such as spun cocoon or shape memory materials having a coil shape or shape memory alloys.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly (phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials, or collagen materials as disclosed in U.S. patent application Ser. No. 12/030,181, filed Feb. 12, 2008, hereby incorporated by reference in its entirety, which discloses collagen materials that may be used for forming a covering. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

In particular, in various embodiments, the device may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly (orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. mPEG imparts malleability to the resulting formulations. In some embodiments, these biopolymers may also be coated on the medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the medical device ranges from about 5 microns to about 250 microns or 5 microns to about 200 microns to delay release from the medical device.

In various embodiments, the medical device comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

The covering material may have functional characteristics. Alternatively, other materials having functional characteristics may be incorporated into the covering. Functional characteristics may include radiopacity, bacteriocidity, source for released materials, tackiness, etc. Such characteristics may be imparted substantially throughout the covering or at only certain positions or portions of the covering.

Suitable radiopaque materials include, for example, ceramics, mineralized bone, ceramics/calcium phosphates/calcium sulfates, metal particles, fibers, and iodinated polymer. Polymeric materials may be used to form the covering and be made radiopaque by iodinating them. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly (lactic acid) (PLA), poly(glycolic acid) (PGA), poly(lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other hysic-chemical properties to enhance drug delivery. In some embodiments, composites of allograft bone and biodegradable polymers (for example, PLEXUR® products available from Osteotech) may be used in the covering.

In some embodiments, the covering may comprise a material that becomes tacky upon wetting. Such material may be, for example, a protein or gelatin based material. Tissue adhesives, including mussel adhesive proteins and cryanocrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

In one embodiment there is a covering comprising two compartments, where first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Mesh Formulations

Any suitable technique may be used for forming a material for the covering. Generally, the material may be formed as a substantially solid material, as a sheet, as a mesh, or in other configuration. In some embodiments, the material may be a textile type material. Thus, for example, the material may be formed using a textile approach such as by weaving, rug making, or knitting. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the covering material, and to perforate it, expand it to create openings, or otherwise make it penetrable by cells, fluids and proteins.

In one embodiment, elongated bone-derived particles or fragments of small intestinal submucosa (for example, approximately 6) may be combined longitudinally into three small bundles, each having, for example, from about 1 to about 3 tissue particles. The three bundles may then be braided. Various methods of braiding and types of braids any of which may be useful in producing the material of the application herein are also described. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed adhering to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of noncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc.

Elongated materials including multistranded materials, e.g., braids, plied yarns, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, e.g., architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be used if cells are to migrate through the mesh. Mesh size may be controlled by physically weaving strands of the material by controlling the ratio of solvent to solids in a precursor material.

Cells may be seeded onto the material, or contained within it. In one embodiment, cells may be encapsulated in a matrix such as alginate or collagen gel and the capsules placed on the material. Seeded materials generally do not need to be incubated for long periods of time in solutions that could partially dissolve the binding agent. Instead, the capsules may be placed on the material or covering shortly before implantation. In another embodiment, cells are simply mixed with a gel, which is then combined with the material. Alternatively, a material or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

Covering Configurations.

The shape, configuration, or form of the covering may be selected for particular applications. Such shape and configuration may include, for example, the basic shape of the covering (e.g., a cylinder, a bag, or a pouch, etc.), whether the covering has a single or a plurality of compartments, and whether the covering includes attachment mechanisms. The covering (or delivery system) may be configured to conform to surrounding bony contours of the space in which it is placed.

As previously discussed, the covering may be formed of as a mesh. Thus, the covering may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures pre-shaped to fit around various implants (e.g. dental, doughnut with hole for dental implants), or relatively elastic ring-like structures that will stretch and then conform to shapes (e.g. rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the substance to be provided within the covering. For example, if the substance to be contained comprises fibers, the covering may be formed as strings or sutures that are wrapped around the fibers.

In certain embodiments, a bone void can be filled. A compartment within the covering material can be at least partially filled with a bone repair substance. In various embodiments, at least partially filled as used herein, can mean that a percentage of the volume of a compartment (or covering material, as applicable) is at least 70% occupied, at least 75% occupied, at least 80% occupied, at least 85% occupied, at least 90% occupied, at least 95% occupied, or 100% occupied. The covering material can be inserted into an opening in the defect until the defect is substantially filled. In various embodiments, a substantially filled as used herein can mean that a percentage of the volume of a defect (or covering material, as applicable) is at least 70% occupied, at least 75% occupied, at least 80% occupied, at least 85% occupied, at least 90% occupied, at least 95% occupied, or 100% occupied. The excess material extending beyond the surface of the bone if the bone were without the defect can then be removed, or at least partially removed such that the opening of the defect is flush with the uninjured bone surface.

A covering as provided herein may further comprise an attachment or coupling mechanism. Any suitable attachment mechanism can be used, such as a tab, loop, tack or other structure adapted for attachment at the site. Also, for example, a covering may include a hook-and-eye (Velcro™) portion. The hook-and-eye portion may be used to couple the covering to a tissue structure, such as bone, or to another covering. For example, a dual compartment covering may be formed by two single-compartment coverings coupled at complementary ends thereof. For example, the coupling portion may comprise overlapping/mating Velcro™ portions. The size and shapes of the single compartment coverings may be the same or may be different. Further, the materials of the compartment coverings and the substances provided therein may be the same or may be different. The coupling may be done pre-implantation or post-implantation. In post-implantation embodiments, the coupling may be done by inserting first and second coverings through an opening into a space and coupling the coverings within the space. Other suitable attachment, or coupling, mechanisms are described more fully below.

In some embodiments, the covering may be labeled. Such labeling may be done in any suitable manner and at any suitable location on the covering. In some embodiments, labeling may be done by using a silk screen printing, using an altered weaving or knotting pattern, by using different colored threads, or other. The labeling may indicate information regarding the covering. Such information might include part number, donor id number, number, lettering or wording indicating order of use in the procedure or implant size.

Compartments

As shown in FIG. 1, the covering 102 may comprise two compartments inside compartment 139 nested into outside compartment 138. While FIG. 1 depicts a covering 101 in a rectangular form, alternate shapes and configurations may be contemplated. In further exemplary embodiments, the covering may be a narrow tube for delivery through a catheter. For example, the covering may be delivered percutaneously using a catheter through which it is inserted. Thus, the covering may have dimensions suitable for receipt in the catheter. Optionally, the covering may be stiffened to facilitate insertion into the catheter. Such stiffening may be achieved through choice of material for the covering, by treating the material of the covering, or other. In some embodiments, the covering may be coated with a material to facilitate sliding engagement with the catheter.

In other exemplary embodiments, a covering may be provided including an elongated containment portion for housing a substance for delivery, and having first and second ends. One or both of the first and second ends may have an attachment mechanism. Any suitable attachment mechanism may be used. For example, the attachment mechanism may have an alternative configuration, such as a bore for receiving a screw. Alternatively, each of the first and second ends may comprise a tab attachment mechanism. One or both of the first and second ends further may be sealed. The seal may comprise a portion of the tab, or may be separate from the tab. The seal may have a width and a thickness suitable for maintaining a seal with the substance provided within the containment portion. In some embodiments, one or both ends may be unsealed such that the covering may be filled with a substance and sealed, for example, via heat sealing, in the operating room.

The elongated containment portion comprises a length, a width, and a cross section. The length may be, for example, approximately 5 cm, approximately 10 cm, approximately 15 cm, approximately 20 cm, or any other suitable length. The width may be, for example, approximately 1 cm, approximately 2 cm, approximately 5 cm or any suitable width. The length to width ratio may vary depending on application. In various embodiments, the covering may have a width of approximately 2.5 cm, a containment portion length of approximately 5 cm or approximately 10 cm, and a tab length of approximately 0.5 cm. In one embodiment, the containment portion may have a generally circular cross-sectional shape with an approximately 1.0 cm diameter. In alternative embodiments, the containment portion may have a generally oval cross-sectional shape. In alternative embodiments, any cross-sectional shape, such as a generally rectangular, generally square, generally star, or any other suitable shape may be used. The length, width, and length-to-width ratio may vary depending on the application for the covering. The exemplary embodiments and dimensions provided above are intended for illustration only and are not limiting.

In one embodiment of a single compartment covering, a plurality of substances may be provided within the covering based on characteristics of the substances. For example, where it is desirable to include a particulated first substance within a material having mesh openings larger than the substance, a second substance may be provided surrounding the particulated first substance to reduce the likelihood of release of particles of the first substance from the mesh. Thus, for example, a particulated first substance and a particulated second substance may be provided wherein the particles of the first substance have a smaller size than the particles of the second substance. A covering is provided comprising a mesh having mesh openings or pores larger than the particles of the first substance. For use, the first substance is provided generally centrally within the covering, the second substance is provided around the first substance and thus between the first substance and the second substance. In further embodiments, the second substance may be coated, for example via spray coating or solvent casting.

In yet a further embodiment, a single compartment covering may be used as a spacer for nonunion. For example, the covering may be placed in a canal of a long bone.

In alternative embodiments, the covering may comprise a plurality of compartments. For example, the covering may comprise nested coverings as illustrated in FIG. 1, coverings coupled via a temporary barrier, coverings separated with a boundary, and others, described below. In embodiments comprising two compartments, a second compartment may be adjacent, apart from, inside, or surrounding a first compartment. Materials for the first compartment and the second compartment (which may be designated first and second substances) may be the same, partially the same, or different. The materials for the first compartment and the second compartment may have different release profiles, different porosities, and other different characteristics. Selection of materials, positioning of the compartments, and other factors relating to the first and second compartments may be chosen to achieve simultaneous or sequential delivery or release of a substance or substances. A first substance may be provided in the first compartment and a second substance may be provided in the second compartment. In some embodiments, an osteoinductive substance may be placed in a compartment generally adjacent tissue being treated as implanted and an osteoconductive substance may be placed in a compartment not adjacent tissue being treated. Release rates for the materials provided in the first compartment and the second compartment may be different. In some embodiments, at least one of the compartments may be unfilled at the time of surgery and autograft, allograft or other material may be provided therein in the operating room or at the surgical site. In some embodiments, the covering may form a 3D scaffold. In some embodiments, each compartment or only some compartments of a multi-compartment device can have an opening at one end, closing member proximate the opening, pre-attached, detachable holding and filling member for filling each compartment with autograft, allograft or other material prior or during surgery, as desired.

For both single and multi-compartment coverings, the covering may be closed after filling substances as discussed above. Accordingly, the covering may be provided in an unfilled, unsealed state as illustrated in FIG. 1. After a substance for delivery is placed in the covering, the covering may be permanently or temporarily closed using a drawstring as depicted in FIGS. 1 to 3 or other closing member. Permanent closure may be, for example, by tying tightly the ends of the drawstring, or the loops of a continuous drawstring, heat sealing, stitching, adhesion, or other methods. Temporary closure may be by tying, fold lock, or cinching. A temporarily closed covering can be opened without damaging the covering during surgical implantation to add or remove substances in the covering.

In some embodiments, at least one but not all of the compartments may be weight-bearing. In other embodiments, all of the compartments may be weight-bearing.

In one embodiment, the covering may comprise a penetrable material at a first compartment configured for placement adjacent bone and a substantially impenetrable material at a second compartment configured for placement adjacent soft tissue. Alternatively, the material of the compartments may have substantially identical characteristics. The covering then can be positioned in any desirable manner. By way of example only, a covering may have a porous surface that is positioned adjacent bone, and a separate or opposite surface that has a generally impenetrable surface that is positioned adjacent soft tissue. Alternatively, a covering may have one compartment that comprises a porous material, and a second compartment that comprises a substantially impenetrable material.

Attachment Mechanisms

The covering may be implanted directly at, near or in the bone defect or optionally be configured with structures to permit attachment at the surgical site, such as to skeletal tissue or to soft tissue structures, or for attachment to other coverings, or for attachment to adjacent implantable medical devices or products (such as a rod or screw or cross-brace of a pedicle screw fixation system, a hip prosthesis, a bone plate, and the like). Generally, the attachment mechanism may be used to retain the covering at the surgical site and any mechanisms capable of doing so may be used. The attachment may be to bone or to adjacent tissues such as muscle, tendon, or ligament. In some embodiments, the attachment mechanism can be made from a biodegradable polymer that is the same or different material than the covering.

Where the covering retains a bone graft substance, the covering may be held in a relatively stable position relative to bone (or relative to the surgical site or surgical defect) to promote bone growth. Accordingly, in some embodiments, the delivery system may be suitable for assisting in attaching tendons, artificial tendons, or ligaments to bone or other structure.

The bone or soft tissue to which the covering is attached may be prepared for receiving the attachment mechanism(s). For example, in spinal applications, slots or perforations may be provided in posterior elements such as transverse processes, spinous processes, or other bone or tissue to receive the attachment mechanism.

Any suitable attachment mechanism may be used, including mechanical, physical, chemical, and biological attachment mechanisms. The attachment mechanism may be provided at an end of the covering, centrally in or on the covering, generally in or on the body of the covering, or any combinations of these. When an attachment mechanism is used to couple first and second coverings to one another, such attachment or coupling may be done pre-implantation or post-implantation. In post-implantation embodiments, the coupling may be done by inserting first and second coverings through an opening into a space and coupling the coverings within the space. In some embodiments, the covering may be provided with attachment mechanisms to facilitate suturing or other attachment of the covering in vivo.

In some embodiments, a covering may include an area for receipt of an attachment mechanism. For example, a covering may include a tab for receipt of a screw. In other embodiments, an attachment mechanism may interface with any portion of the covering. For example, a screw attachment mechanism may be threaded through a covering at any location, including central to a containment area of the covering. In some embodiments, a screw attachment mechanism may be threaded through the covering and the substance provided in the containment area of the covering.

A further method of attachment may comprise suturing or otherwise attaching the covering to a tether, anchor, or screw embedded in a bony structure, e.g. a pedicle screw of a spinal stabilization system. Such screw, anchor, or tether may pass through the covering and its contained contents to provide fixation, or through a tab at a margin of the covering, or through other structure of the covering.

Chemical attachment mechanisms may comprise, for example, a bioadhesive or glue, cement, tape, tissue adhesives, or similar mechanism. Chemical attachment mechanisms may further comprise mechanisms that facilitate cross-linking. In further embodiments, attachment mechanisms such as crimping, welding, soldering, or brazing may be used. For example, tissue welding may be used. Further, attachment may be achieved via friction.

Suitable adhesives for use may include, for example, cyanoacrylates (such as histoacryl, B Braun, which is n-Butyl-2 Cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; e.g., in some circumstances, a temporary adhesive may be desirable, e.g., for fixation during the surgical procedure and for a limited time thereafter, while in other circumstances a permanent adhesive may be desired. Where the compartment is made of a material that is resorbable, the adhesive can be selected that would adhere for about as long as the material is present in the body. In some embodiments, the covering material may be treated to form chemical linkages between the covering and adjacent tissue, whether bone or soft tissue.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms.

In some embodiments, the covering can comprise edges having polymers that are more hydrophilic than the polymers in other areas of the covering (e.g., body). In this embodiment, the covering, when implanted, will draw bodily fluid to this area more so than in other areas and this will cause the edges of the covering to expand and anchor the covering at, near or in the defect site. Alternatively, the body of the covering can have polymers that are more hydrophilic than the polymers in the edges of the covering. In this embodiment, the covering, when implanted, will draw bodily fluid to the body area more so than the edges and this will cause the body of the covering to expand and anchor the covering at, near or in the defect site.

Generally, any combination of mechanical, physical, chemical, or biological attachment mechanisms may be used.

Any of the various attachment mechanisms may be provided as part of the covering or may be supplied separately. In various embodiments, the attachment mechanisms may be integral to the covering. Alternatively, the attachment mechanisms may be secured to the covering, for example, by stitching, welding, crimping, or other. The attachment mechanisms may have any suitable geometric configuration and may optionally include apertures for receiving other components for coupling in vivo, such as an aperture for receiving a screw. Thus, for example, an attachment mechanism may be provided configured for receiving an anchor for fixation to bone. Generally, any number of attachment mechanisms may be provided at any suitable location on the covering.

The attachment mechanisms may be manufactured of the same material as the portion of the covering to which it is coupled or may be manufactured of a different material from the portion of the covering to which it is coupled. The attachment mechanism may be resorbable or nonresorbable. The material of the attachment mechanism may be selected to allow anchoring the covering to an adjacent covering having a complementary attachment mechanism or to another structure. In various embodiments, the attachment mechanism may comprise, allograft, synthetic materials, demineralized bone, nondemineralized bone, other material, or combinations of these. The shape and size of the attachment mechanism may be selected based on application.

In some embodiments, the covering may be tubular and have threaded ends such that the ends may be threaded with a reciprocal thread of a further device or implant. For example, the covering may be used with interference screws. In some embodiments, the covering may include extensions or tabs that may be used for wrapping around or suturing to the surgical site. Alternatively, the covering may be sutured directly to the surgical site. The ends of the covering may be presealed or may be sealed after introduction of contents. Sealing may be done by using adhesives, heating, solvent treatment, suturing, knotting, or any other means.

Bioactive Agents

A substance is provided inside the covering, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The covering may be used to deliver a substance comprising any suitable biocompatible material. In specific embodiments, the covering may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in the covering include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the covering. A substance provided within the covering may be homogenous, or generally a single substance, or may be heterogeneous, or a mixture of substances.

In some embodiments, the covering can comprise one or more compartments having demineralized bone material therein. The demineralized bone material can be comprise demineralized bone, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the covering may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the covering comprises elongated demineralized bone fibers having an average length to average thickness ratio or aspect ratio of the fibers from about 50:1 to about 1000:1. In overall appearance the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

In some embodiments, the covering comprises elongated demineralized bone fibers and chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the biocompatible material comprises demineralized bone matrix fibers and demineralized bone matrix chips in a 30:60 ratio.

In some embodiments, the demineralized bone material can be in the covering and comprises from about 1 to about 70 micrometers particle size range or from about 125 to about 250 micrometer particle size range.

In some embodiments, the covering may have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$. After the cover is administered to the target site, the covering may have a modulus of elasticity in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In some embodiments, the substance may be designed to expand in vivo. Such an embodiment may be used to fill a space and create contact with congruent surfaces as it expands in vivo, for example for interbody fusion. Thus, in some embodiments, the delivery system may be used in the disc space, between implants, or inside a cage.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules;

vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; antiemetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of a covering comprising two compartments, a first growth factor may be provided for delivery by the first compartment and a second growth factor may be provided for delivery by the second compartment. The first and second growth factors may be provided with other substances. The first and second growth factors may be selected (and placed in respective compartment for positioning in vivo) based on desired characteristics of the growth factor. For example, an angiogenic growth factor may be provided in the first compartment and an osteoinductive growth factor may be provided in the second compartment.

Similarly, the substance delivered by the first compartment and the substance delivered by the second compartment may be selected based on desired characteristics of the compartment according to its placement in vivo. Thus, for example, one compartment may have a substance that is substantially osteoclast stimulating while another compartment may have a substance that is substantially osteoblast stimulating.

In one embodiment, demineralized bone fibers may be provided in the first compartment and surface demineralized bone chips may be provided in the second compartment. In this embodiment, the demineralized bone fibers may generally provide osteoinductive characteristics and the surface demineralized chips may generally provide osteoinductive and/or osteoconductive characteristics. In use, the covering may be laid flat on the transverse process and positioned such that the first compartment, holding the demineralized bone fibers, is nearest the vertebral body and the second compartment, holding the surface demineralized bone chips, is farther from the vertebral body, or the compartments may be positioned in any other desired configuration. In another embodiment, a covering may comprise first and second compartments wherein autograft may be placed in one of the compartments prior to placement of the covering in vivo, described more fully below. In other embodiments, three or more compartments may be used, as appropriate for the materials being delivered and the application of the compartmented implant. More than one substance may be provided in a compartment. For example, surface demineralized bone chips and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In some embodiments, other medical devices may be provided within the covering. For example, one or more electrical stimulator electrodes may be provided within the covering.

Sterilization

The medical device and/or covering may be sterilizable. In various embodiments, one or more components of the medical device and/or covering are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device and/or covering. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device and/or covering. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device and/or covering is included in a gel.

Other methods may also be used to sterilize the device and/or covering and/or one or more components of the device and/or covering, including, but not limited to, gas sterilization, such as, for example, with ethylene oxide or steam sterilization.

Methods of Use

The covering delivers the substance or substances in vivo. Such delivery may be active, passive, by diffusion, or other. Active delivery may include the degradation or decomposition of the covering with the interaction of body fluids, extracellular matrix molecules, enzymes or cells. It may also include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The covering is loaded with the substance for placement in vivo. The covering may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Any other suitable method may be used for loading a substance in the covering in the operating room or at the surgical site. For example, the substance may be spooned into the covering, the substance may be placed in the covering using forceps, the substance may be loaded into the covering using a syringe (with or without a needle), or the substance may be inserted into the covering in any other suitable manner. Specific embodiments for loading at the surgical site include for vertebroplasty or for interbody space filler.

In this application, in various embodiments, loading in the operating room or at the surgical site can be done with any of these materials and further with autograft and/or bone marrow aspirate by adding the desired material through the filling member or funnel 150 by gravity using a spoon and/or a plunger to push the material through. For example, the surgeon can grasp the covering or bag 102 depicted in FIG. 1 with his/her fingers at the finger grips 142, hold it steadily by pre-attached collar 120 and proceed to load the bag via funnel 150 through opening 112 of covering 102. Thereafter, once covering 102 is full, pre-attached detachable collar 120 and funnel 150 can be removed and pre-attached drawstring(s) 114 are pulled until the covering is closed and the drawstrings are tied and knotted.

For placement, the substance or substances may be provided in the covering and the covering placed in vivo. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion.

In continuous tube embodiments, the surgeon may divide the tube into the desired number of compartments, using a crimper, heat tool or other. Alternatively, in an embodiment wherein the tube is perforated into a plurality of compartments, the surgeon may select the number of compartments desired and cut along the applicable perforation. In some embodiments, some of the compartments may be prefilled with a substance for delivery and other compartments may be empty for filling by the surgeon. For example, ever other compartment between perforations may be preloaded or filled. The osteoimplant thus may be customized by filling the empty compartments with a desired substance.

Attachment mechanisms provided on the covering may be used to couple the covering to a site in vivo.

The covering may be used in any suitable application. In some embodiments, the covering may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The delivery system may be used in a minimally invasive procedure via placement through a small incision, via delivery through a tube, or other. The size and shape may be designed with restrictions on delivery conditions. In some embodiments, pieces of the covering can be separated by pulling or tearing force applied along separation assists if present in a multi compartment configuration and the pieces of the covering can be used to surround the bone defect. For examples, 3 pieces of the torn covering can be placed around the bone defect to triangulate bone growth by the influx of cells, in, at or near the bone defect.

In some embodiments, the covering is flexible enough so that the covering can be folded upon itself before it is implanted at, near or in the bone defect.

An exemplary application for using a delivery system as disclosed is fusion of the spine. In clinical use, the covering and delivered substance may be used to bridge the gap between the transverse processes of adjacent or sequential vertebral bodies. The delivery system may be used to bridge two or more spinal motion segments. The covering surrounds the substance to be implanted, and contains the substance to provide a focus for healing activity in the body.

In other applications, the delivery system may be applied to transverse processes or spinous processes of vertebrae.

Generally, the delivery system may be applied to a preexisting defect, to a created channel, or to a modified defect. Thus, for example, a channel may be formed in a bone, or a pre-existing defect may be cut to form a channel, for receipt of the delivery system. The covering may be configured to match the channel or defect. In some embodiments, the configuration of the covering may be chosen to match the channel. In other embodiments, the channel may be created, or the defect expanded or altered, to reflect a configuration of the covering. The covering may be placed in the defect or channel and, optionally, coupled using attachment mechanisms.

At the time just prior to when the delivery system is to be placed in a defect site, optional materials, e.g., autograft bone marrow aspirate, autograft bone, preparations of selected autograft cells, autograft cells containing genes encoding bone promoting action, can be combined with the covering and/or with a substance provided within the covering prior to or during the surgical procedure. The osteoimplant can be implanted at the bone repair site, if desired, using any suitable affixation member, for example, sutures, staples, bioadhesives, screws, pins, rivets, other fasteners and the like or it may be retained in place by the closing of the soft tissues around it.

Although the invention has been described with reference to preferred embodiments, persons skilled in the art will recognize that changes may be made in form and detail without departing from the spirit and scope of the invention.

What is claimed is:

1. A delivery system comprising a biodegradable covering configured for implantation into a bone defect site, the covering having at least one compartment, the at least one compartment defining an opening having a pre-attached closing member, a pre-attached detachable holding member surrounding the opening of the at least one compartment and a pre-attached removable filling member configured to fit within the opening of the at least one compartment for loading the at least one compartment with at least one substance, wherein the pre-attached detachable holding member includes a collar, wherein the detachable collar includes a gripping member comprising least two finger grips or finger depressions or a combination thereof.

2. A delivery system according to claim 1, wherein the pre-attached removable filling member includes a funnel, a spoon, a syringe or a combination thereof.

3. A delivery system according to claim 1, wherein the gripping member is detachable from the collar or is part of the collar.

4. A delivery system according to claim 3, wherein the closing member is cooperatively attached with the gripping member, such that the at least one compartment is closed upon disengaging the gripping member from the collar.

5. A delivery system according to claim 3, wherein the collar, the gripping member or the funnel or all include injected molded plastic or a material selected from bioerodible polymers, bioabsorbable polymers, biodegradable biopolymers, synthetic polymers, copolymers or combinations thereof.

6. A delivery system according to claim 1, wherein the collar is pre-attached to the proximal surface of the covering or the at least one compartment through pull-string sutures or compression fittings or a combination thereof.

7. A delivery system according to claim 1, wherein the closing member includes a drawing string, stitches, sutures, a heat seal, an adhesive seal, a pressure fitting or a combination thereof.

8. A delivery system according to claim 7, wherein the drawstring is slidably received in a casing extending about the periphery of the opening of the at least one compartment and comprises two openings positioned proximate to each other so that when end portions of the drawstring are pulled out of the drawstring casing through the two apertures, the periphery of the at least one compartment gathers to reduce the opening of the at least one compartment in size sufficiently to enclose the at least one substance therein.

9. A delivery system according to claim 1, wherein the at least one substance comprises autograft, allograft, demineralized bone matrix fibers, or demineralized bone matrix chips in a 30:60 ratio or a combination thereof.

10. A delivery system according to claim 9, wherein the collar, the gripping member, the funnel or all include injected molded plastic or a material selected from bioerodible polymers, bioabsorbable polymers, biodegradable biopolymers, synthetic polymers, copolymers or combinations thereof.

11. A delivery system comprising a covering configured for implantation into a bone defect site, the covering having at least one compartment comprising an elongated containment having a first end and a second end opposite each other, wherein one end defines an opening, the containment having a closing member proximate the opening, a pre-attached detachable holding member surrounding the opening of the containment, the pre-attached holding member including a gripping member and a pre-attached removable filling member configured to fit within the opening of the elongated containment, wherein the pre-attached detachable holding member includes a collar, wherein the detachable collar includes the gripping member comprising least two finger grips or finger depressions or a combination thereof.

12. A delivery system according to claim 11, wherein the pre-attached detachable holding member includes a collar configured to receive the implantable covering around the opening of the implantable cover proximate the closing member.

13. A delivery system according to claim 11, wherein the gripping member comprises finger depressions or finger grips on either side of the collar.

14. A delivery system according to claim 11, wherein the pre-attached removable filling member configured to fit within the opening of the elongated containment comprises a funnel.

* * * * *

UNITED STATES PATENT AND TRADEMARK OFFICE
CERTIFICATE OF CORRECTION

PATENT NO. : 9,241,797 B2  
APPLICATION NO. : 14/582600  
DATED : January 26, 2016  
INVENTOR(S) : McKay It is certified that error appears in the above-identified patent and that said Letters Patent is hereby corrected as shown below:

In the specification,

In Column 1, Line 6, delete "2012," and insert -- 2012, now Pat. No. 8,926,622, --, therefor.

In Column 7, Line 18, delete "not" and insert -- no --, therefor.

In Column 10, Line 9, delete "bacteriocidal" and insert -- bactericidal --, therefor.

In Column 14, Line 4, delete "bacteriocidal" and insert -- bactericidal --, therefor.

In Column 14, Lines 19-20, delete "morphogenic" and insert -- morphogenetic --, therefor.

In Column 14, Line 34, delete "hysic-chemical" and insert -- physic-chemical --, therefor.

In Column 14, Line 42, delete "cryanocrylates," and insert -- cyanoacrylates, --, therefor.

In Column 25, Line 21, delete "morphogenic" and insert -- morphogenetic --, therefor.

In the claims,

In Column 29, Line 15, in Claim 1, delete "least" and insert -- at least --, therefor.

In Column 30, Line 10, in Claim 9, delete "30:60 ratio" and insert -- ratio of from 25:75 to 75:25 --, therefor.

In Column 30, Line 29, in Claim 11, delete "least" and insert -- at least --, therefor.

Signed and Sealed this  
Twenty-fourth Day of May, 2016

Michelle K. Lee  
*Director of the United States Patent and Trademark Office*